US007005629B2

(12) United States Patent
Flem

(10) Patent No.: US 7,005,629 B2
(45) Date of Patent: Feb. 28, 2006

(54) SYSTEM FOR STEREO-VIEW BASED DETECTION OF FEATURES OF ARTICLES

(75) Inventor: Lennart Flem, Kolsås (NO)

(73) Assignee: Tomra Systems ASA, Asker (NO)

(*) Notice: Subject to any disclaimer, the term of this patent is extended or adjusted under 35 U.S.C. 154(b) by 137 days.

(21) Appl. No.: 10/466,892

(22) PCT Filed: Jan. 22, 2002

(86) PCT No.: PCT/NO02/00029

§ 371 (c)(1),
(2), (4) Date: Jul. 21, 2003

(87) PCT Pub. No.: WO02/058856

PCT Pub. Date: Aug. 1, 2002

(65) Prior Publication Data
US 2004/0114136 A1   Jun. 17, 2004

(30) Foreign Application Priority Data
Jan. 23, 2001 (NO) ................................. 20010407

(51) Int. Cl.
G01N 9/04 (2006.01)
G06M 7/00 (2006.01)
H01J 40/14 (2006.01)

(52) U.S. Cl. ............... 250/223 B; 356/427; 250/223 R

(58) Field of Classification Search ........... 250/223 B, 250/223 R, 221, 222.1, 559.4, 559.21, 559.22; 356/427–428, 240.1; 209/509, 522, 524–525, 209/576–577
See application file for complete search history.

(56) References Cited

U.S. PATENT DOCUMENTS

| 4,429,998 A | * | 2/1984 | Carson et al. ............... 356/428 |
| 4,868,901 A | * | 9/1989 | Kniskern et al. ........ 250/222.2 |
| 5,448,078 A |   | 9/1995 | Nakazawa |
| 5,896,195 A | * | 4/1999 | Juvinall et al. .......... 356/240.1 |
| 6,078,038 A | * | 6/2000 | Cooper .................... 250/208.1 |
| 6,104,482 A | * | 8/2000 | Brower et al. ........... 356/239.4 |
| 6,275,287 B1 | * | 8/2001 | Watanabe ................ 356/239.4 |

FOREIGN PATENT DOCUMENTS

| DE | 3240596 A1 | 5/1984 |
| EP | 1118854 A1 | 7/2001 |
| GB | 2288016 A | 10/1995 |
| WO | WO 0049582 | 8/2000 |

* cited by examiner

Primary Examiner—David Porta
Assistant Examiner—Patrick J. Lee
(74) Attorney, Agent, or Firm—Rodman & Rodman

(57) ABSTRACT

An optical system having a light source means and a detector means for detecting one or more articles which by means of a conveyor move or are temporarily stationary under the means, where said article(s) has/have at least one reflective portion, and where light is emitted towards the article(s) from the light source means and reflected back towards the detector means. The optical system is characterised in that at a distance above the conveyor there is provided a lens, that the light source means and the detector means are located in or essentially in the same plane which is parallel to the plane of the lens and coincident with the focal plane of the lens, and that the optical axis of the lens is coincident with an axis perpendicular to the focal plane and located halfway between the light source means and the detector means.

16 Claims, 6 Drawing Sheets

FIG. 1
FIG. 2
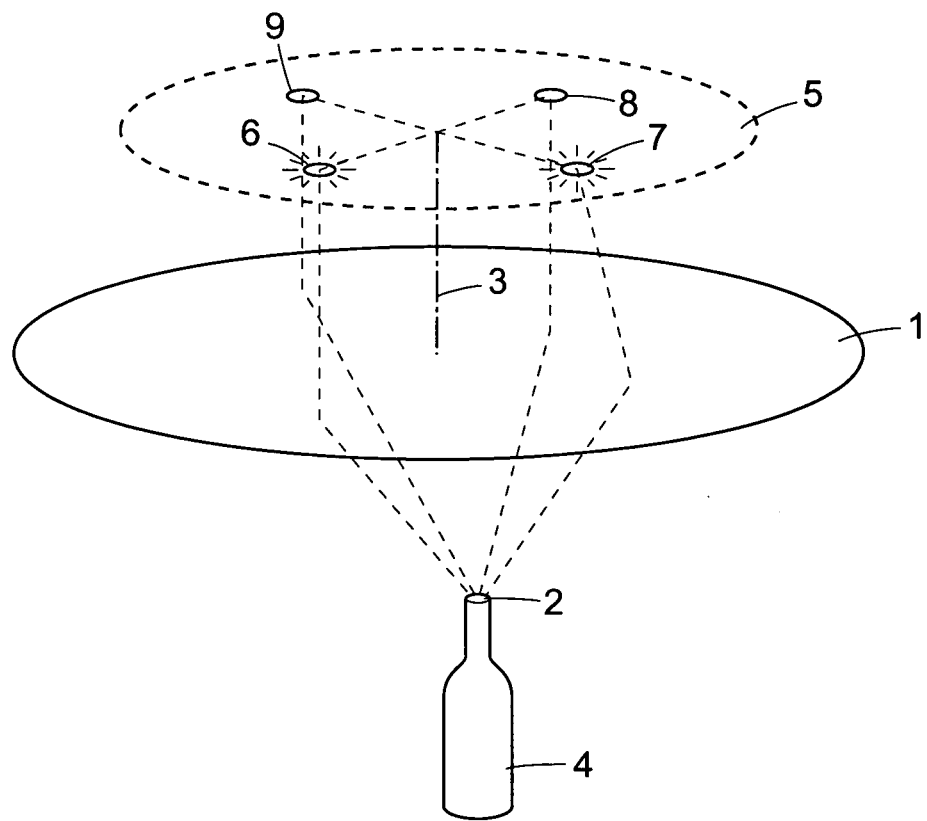
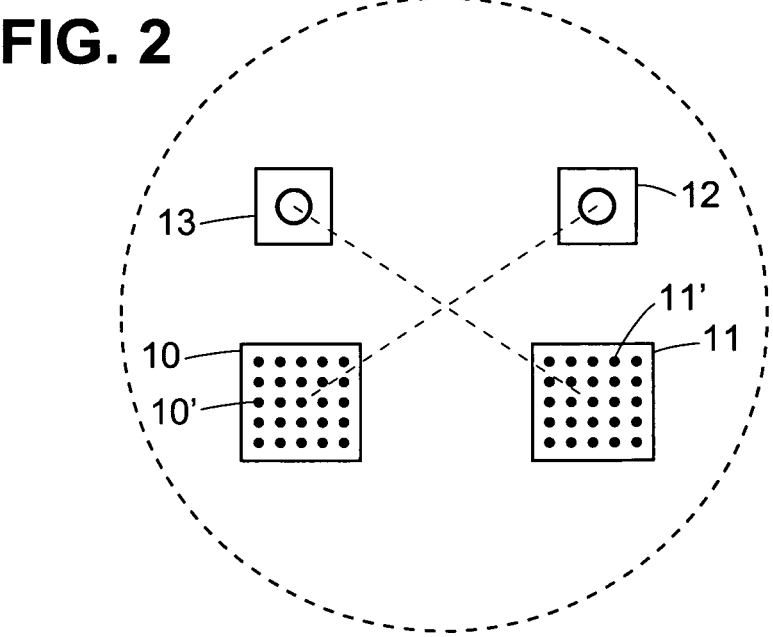

SYSTEM FOR STEREO-VIEW BASED DETECTION OF FEATURES OF ARTICLES

The present invention relates to an optical system having a light source means and a detector means for detecting one or more articles which by means of a conveyor move or are temporarily stationary underneath the means, where said article(s) has/have at least one reflective portion, and where light is emitted towards the article(s) from the light source means and is reflected back towards the detector means.

In particular when detecting articles such as bottles in bottle crates, it is often difficult to obtain an unambiguous definition of each individual bottle in the crate, its size and type. This is due to the fact that such bottles must normally be viewed from above down towards the crate, and often whilst the crate is in motion.

The present invention is based on the use of an optical system wherein specular reflections from all the bottles in a bottle crate will be visible to a camera when the light source is defined and is preferably point shaped. By having several pairs each consisting of a camera and a light source, the present optical system will be able to provide depth of view by using disparity measurements, whereby it will be possible to measure, for example, the height of the bottles and also of the crate.

According to the invention, the optical system is characterised in that at a distance above the conveyor there is provided a lens, e.g., a Fresnel lens, that is common to the light source means and the detector means, that the light source means and the detector means are located in or essentially in the same plane which is parallel to the plane of the lens and coincident with the focal plane of the lens, and that the optical axis of the lens is coincident with an axis perpendicular to the focal plane and lying halfway between the light source means and the detector means. This and additional embodiments of the optical system will apparent from the attached patent claims and from the following description with reference to the attached drawings.

FIG. 1 is a drawing showing the principle of the optical system according to the invention.

FIG. 2 shows by way of example two light source/camera pairs.

FIG. 5b shows a detail of the light source/camera lens pairs of FIG. 5a.

Figure 3:
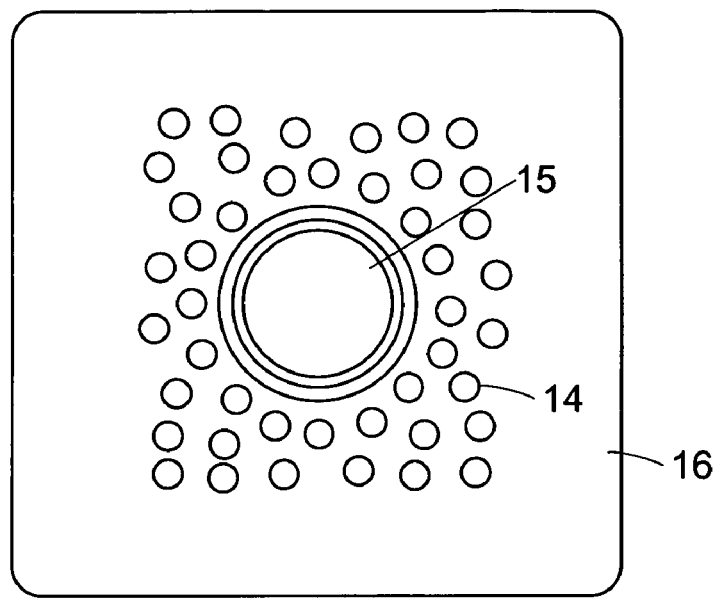
FIG. 3 shows a variant of the combination of light source and camera

Basically, the system consists of a lens 1, for example, a Fresnel lens, and where a reflective face 2 which is perpendicular to the axis 3 of the lens 1 is formed by the reflective top 2 of a bottle 4. The reflective top 2 of the bottle is on one side of the lens 1 and the focal plane 5 of the lens is on the other side of the lens 1. When light is emitted from a location 6 or 7 in the focal plane, it will by means of the specular effect from the reflective top of the bottle be focused on another point in the focal plane, just as far off the lens axis 3, but on the opposite side thereof, and where a respective camera 8 and 9 is located. Thus, the top of the bottle will be imaged in respective camera 8 or 9. No other specular, direct reflection will be able to hit the camera. Height measurement can be done in many ways, for example, by comparing images taken from different points in the focal plane and looking at the disparity of the top of the bottle in the different images, thereby easily allowing an analysis of the bottle height to be made on the basis of standard criteria which have been entered in the system. The light source means will normally consist of n light sources and the detector means will likewise consist of n cameras, where $n \geq 1$. When $n \geq 2$, all the pairs, each consisting of one light source and one camera, will be in the same focal plane of lens 1, like the light source 6 and the camera 8, and the light source 7 and the camera 9, and it will be seen in particular from FIG. 1 that a point halfway between the light source and the camera in each pair is on the optical axis 3 of the lens.

Figure 4:
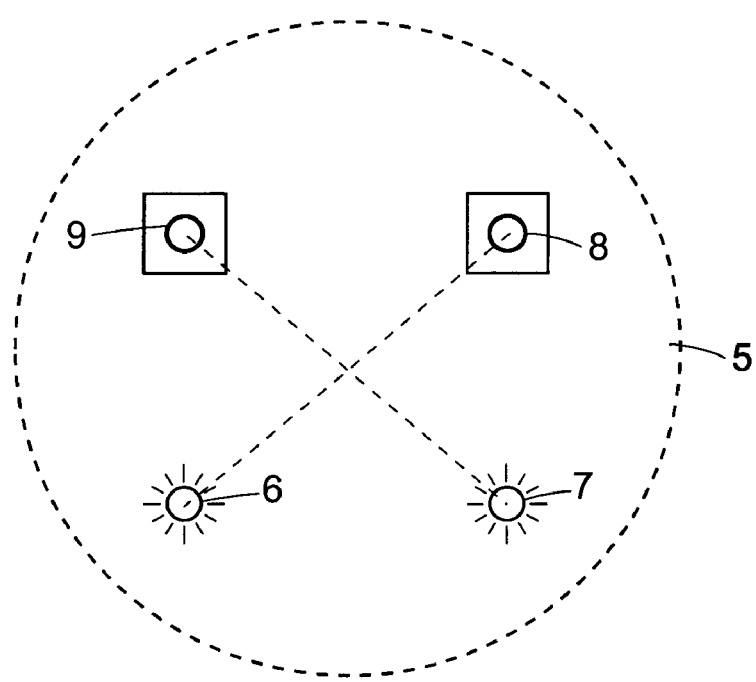
FIG. 4 shows a further variant of two pairs each consisting of a light source and a camera.

In the illustrated example in FIG. 1 and also in FIG. 4, the light source is preferably a point shaped light source. However, it is conceivable, as shown in FIG. 2, that the light source, indicated by the reference numerals 10 and 11 in this figure for respective light source/camera pairs 10, 12 and 11, 13, consists of a plurality of light points 10' and 11' respectively. When the light source 10 and thus the camera 12 are active, it is possible that some, but not all of the light points 10' are activated, or at least some of the light points 10' are adapted to emit light that is coloured or to emit light of different colours and/or light intensity. The same can be provided for the light points 11' when the light source 11 and the detector in the form of the camera 13 are activated.

In FIG. 3 it is shown that the light source, in this case consisting of a plurality of light points 14, can surround a camera lens 15 in a unit 16. Optionally, the light source may consist of an annular body, or the annular body may in fact be formed of a plurality of light points 14. The light points 14 will be related to a camera lens that is located on a unit corresponding to unit 16, but diagonally relative to the optical axis of the lens. Similarly, the lens 15 will be related to a light source, for example, in the form of light points 14 on the second (non-illustrated) unit which corresponds to the unit 16.

FIG. 4 shows a solution similar to that shown in FIG. 1 in more detail and therefore the same reference numerals are used as in FIG. 1.

Figure 5A:
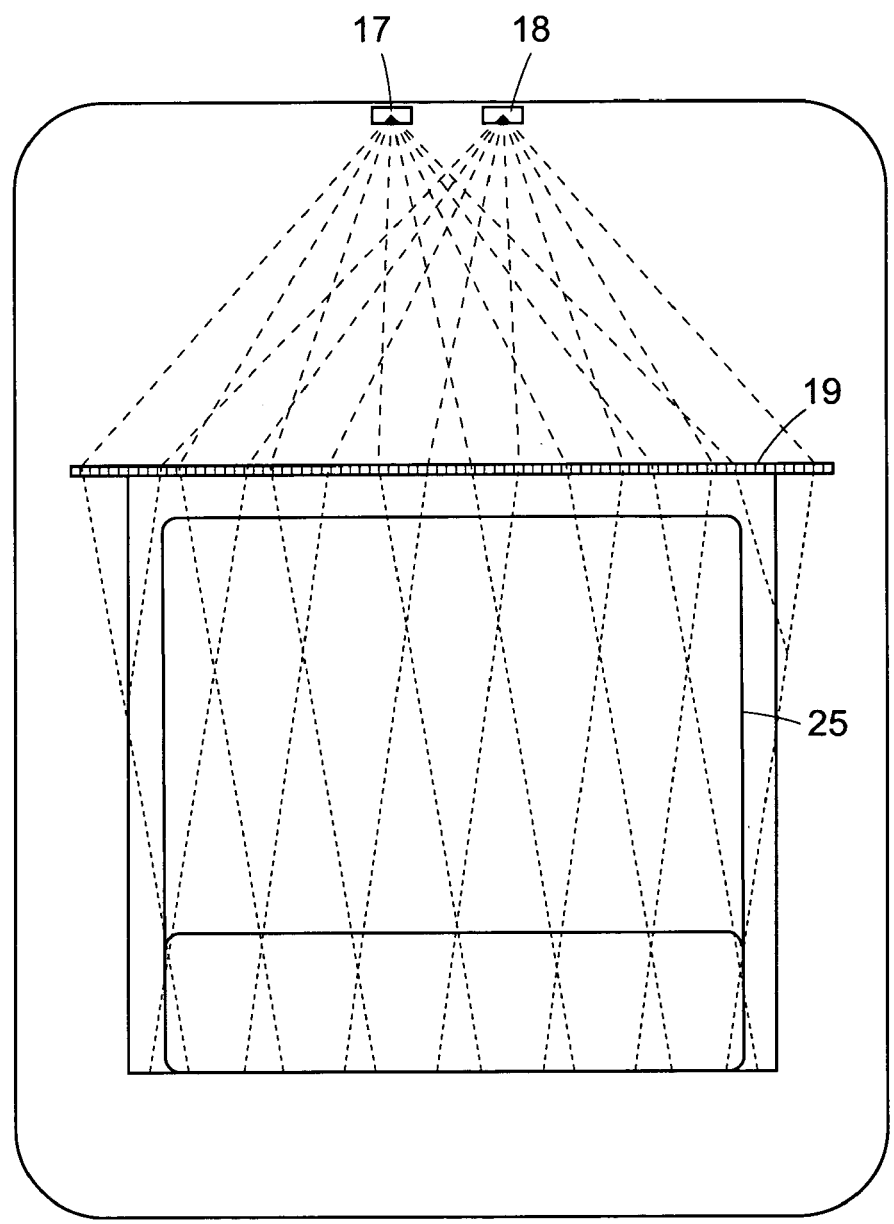
FIG. 5a shows an optical system consisting of two cameras and two light sources in cooperation with one lens.

FIG. 5a shows an array of two light source/camera pairs, like the pairs 6, 8 and 7, 9 shown in FIG. 1 and FIG. 4 or the pairs 10, 12 and 11, 13 in FIG. 2 or a solution as shown in FIG. 3 where the light source surrounds a lens of a camera, the light source in the first of the pairs surrounding the camera lens in a second pair, and the light source in the second pair surrounding the camera lens in the first pair. As will be seen in FIG. 5a, the two light source/camera pairs, as indicated by the reference numerals 17, 18 are behind the same lens 19, in the focal plane of the lens 19, but on their respective sides of the optical axis of the lens. The height of articles, such as bottles in a case, is calculated as is done traditionally in a stereoview system. Such stereoview systems are generally known from a number of publications.

Figure 5B:
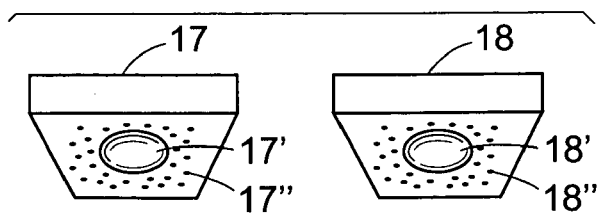

FIG. 5b show the constituents of the respective light source/camera pairs 17 and 18 to include respective cameras 17" and 18".

All light coming from a light source and hitting a horizontal reflecting face, such as a reflective top of a bottle, will hit the aperture of the camera located on the opposite side of the optical axis. As shown in FIG. 5a, both long sides of a bottle case will be imaged and allow the possibility of logo recognition by using a separate light source to improve the illumination, as shown in more detail in FIG. 7, for example, by using a supplementary light source 20. However, it is also conceivable that at a point laterally displaced from and along the movement path of the case, there is provided an alternative light source 21 and/or an inclined mirror body 23 viewable by a camera (as for instance, the camera 22), so that via said mirror body there is the possibility of viewing a side portion 24 of a bottle crate 25 more clearly. It is also possible that a light source 26, such as that shown in dotted lines, can be located on the upper side of the lens 27 and made to emit light towards a partially transparent reflective face 28 so as to better illuminate the sides of the crate 25.

Figure 6:
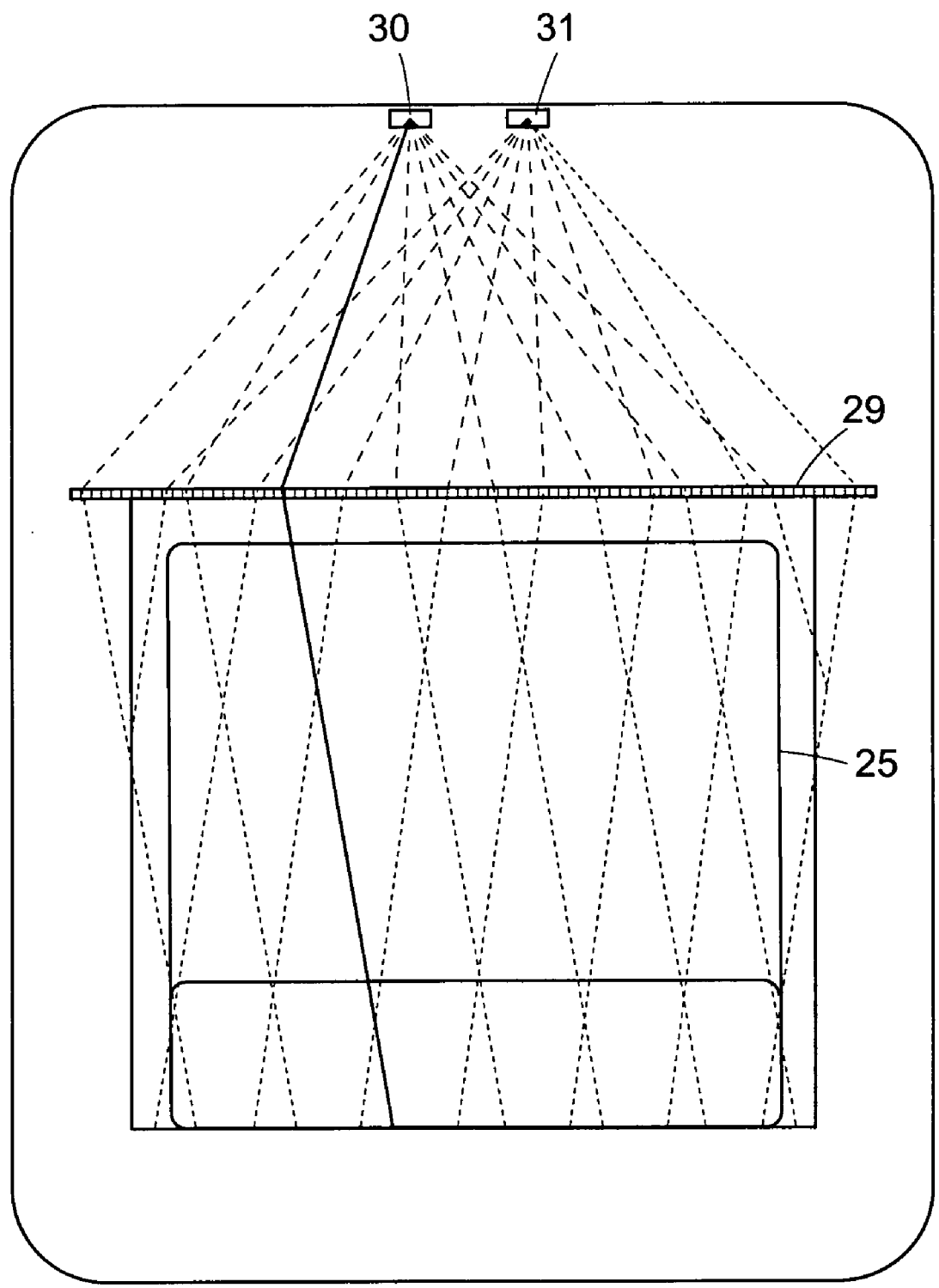
FIG. 6 shows a variant with a lens, and one camera and one light source.

The variant shown in FIG. 6 is based on a light source and a camera behind the same lens, indicated in the figure by the reference numeral 29. The light source is indicated in the figure by the reference numeral 30, and the camera is indicated by the reference numeral 31. A slit (not shown) which is rotated in front of the light source, preferably a point source, will provide a moving light plane at a constant angle. All light that hits a horizontal, reflective face, such as a reflective face on the top of a bottle, will be able to hit the camera aperture of the camera 31. Depth of view can then be produced by triangulation given that the position of the light plane is known at the time of imaging. The system is oriented so that the light plane scan takes place perpendicular to the conveyor direction in order to obtain a minimum scanning field and the possibility of logo recognition on the bottle crate 25.

Figure 9:
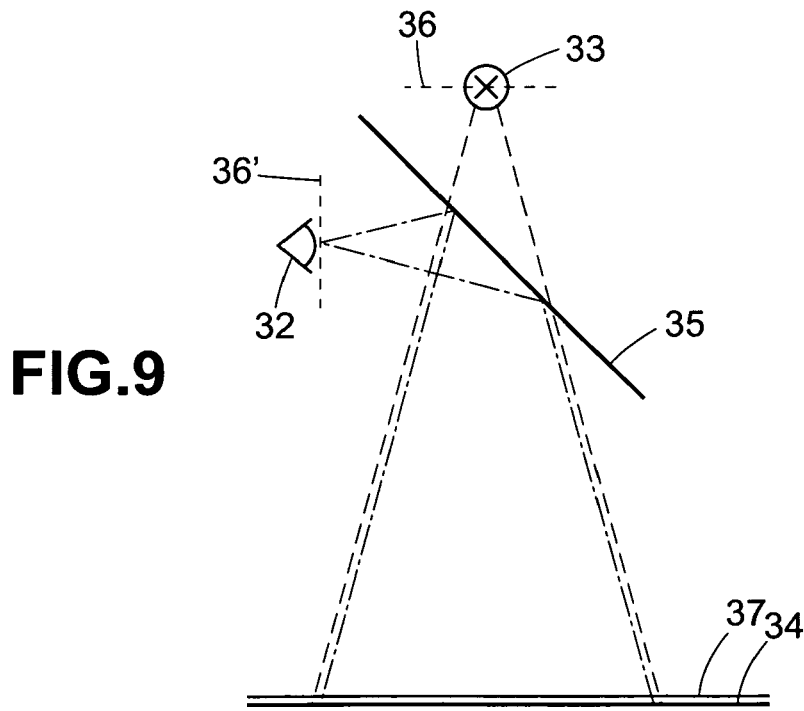
FIG. 9 shows a variant with regard to the location of the light source and camera.

In certain instances, as indicated in FIG. 9, it may be expedient to use an inclined, partially transparent mirror 35 in the light path from a light source means 33, and where the detector means, indicated by the reference numeral 32 in the figure, receives reflected light from an article via said mirror 35. The detector 32 and the light source 33 will be at different physical distances from the lens 34, but nevertheless at the same optical distance from the lens 34 and thus in respective focal planes 36, 36'.

As indicated in the drawings, the respective light source and camera in each pair have approximately equal aperture angles. In most cases this is essential in order to obtain optimal measurement data. Although the lens, such as the lens 1, 19, 29 and 34 may be a Fresnel lens, other types of lenses may also be used. However, it will be desirable that the lens is provided with an antireflection coating, schematically indicated in FIG. 9 by the reference numeral 37. However, it will be appreciated that this antireflection coating, which is to prevent the lens itself from being perceived as the reflective face, will be extremely thin.

Figure 7:
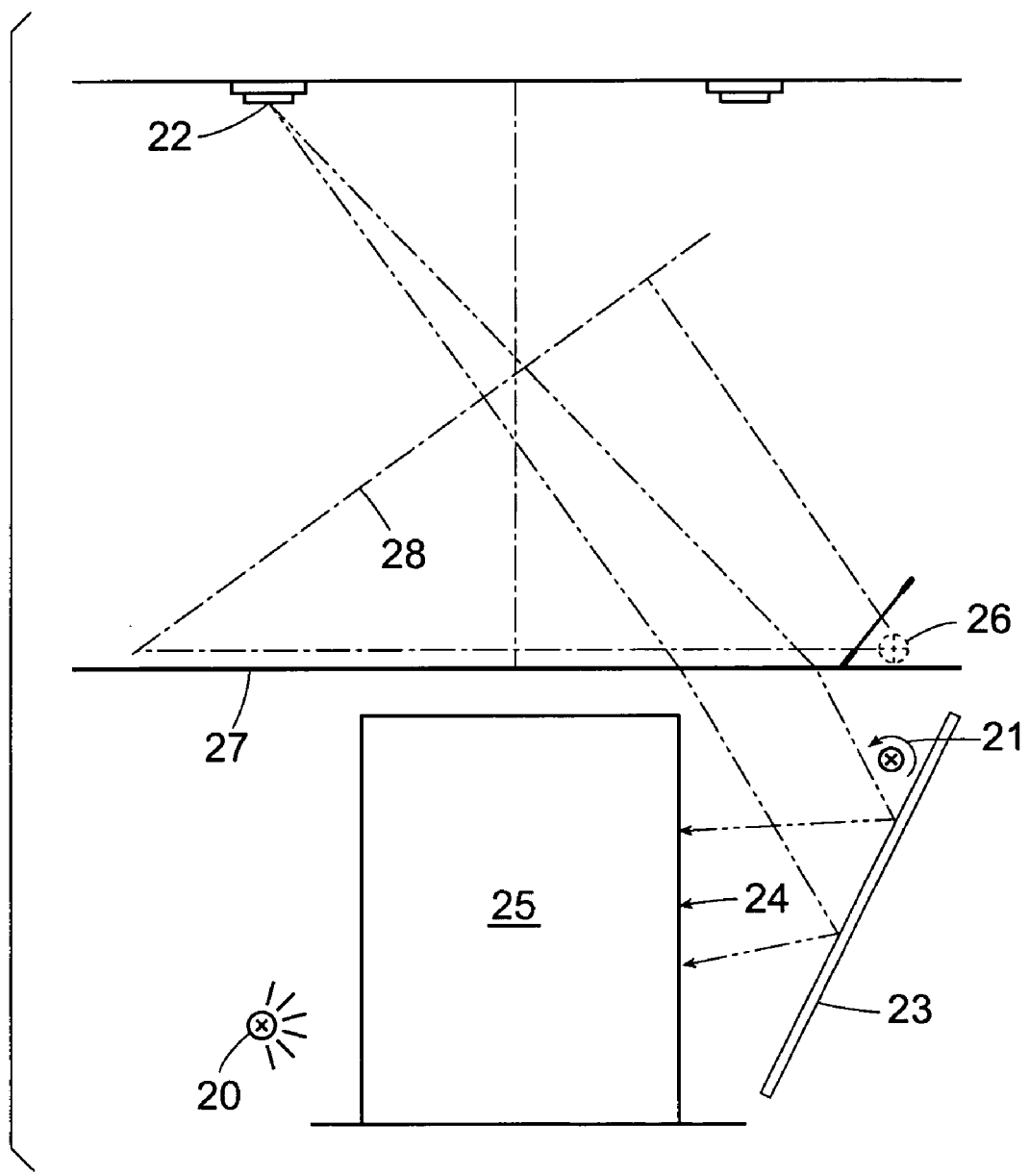
FIG. 7 shows a solution for viewing the side portion of a case.
Figure 8:
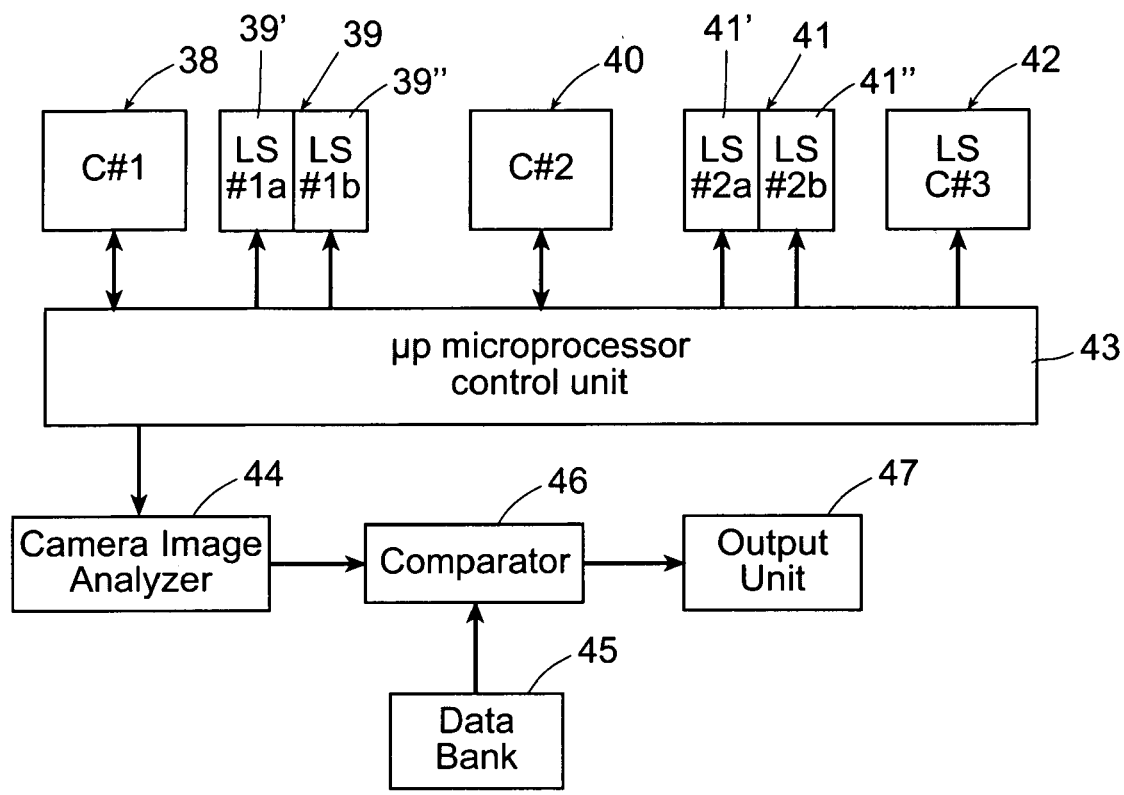
FIG. 8 is a simplified block diagram of function blocks that are incorporated in the optical system according to the invention.

In FIG. 8, by way of example, two light source/camera pairs are indicated by the reference numerals 38, 39 and 40, 41. The units 38, 39 are located diagonally relative to the optical axis 3 of the lens and the same applies in the case of the units 40, 41. Optionally, as indicated in connection with, for example, FIG. 2, the light source 39 can be split into a first light source member 39' and a second light source member 39". The same may be the case for the light source 41 with light source members 41' and 41". If there is a need for any more light sources, as for instance one or more of the light sources 20, 21 or 26, as shown in FIG. 7, such a light source is indicated in FIG. 8 by the reference numeral 42. The light sources and the cameras can be controlled from a microprocessor 43. A camera image analyser (CIA) 44 is connected to the microprocessor 43. A data bank 45 is provided in which certain standard image definitions are stored. A comparator 46 compares the output from the units 44 and 45 and outputs these to an output unit 47 which gives a definition of the article or articles that are detected by the optical system.

Further modifications of the optical system as taught within the scope of the attached patent claims are of course possible within the scope of the invention. The preceding illustrative exemplary embodiments of the invention are merely to be seen as examples, and should not be understood as in any way restricting the scope of the invention.

What is claimed is:

1. An optical system having a light source means and a detector means for detecting one or more articles which by means of a conveyer move or are temporarily stationary under the light source means and detector means, where said article(s) has/have at least one reflective portion, and where light is emitted towards the article(s) from the light source means and reflected back towards the detector means, characterized in that at a distance above the conveyor there is provided a lens that is common to the light source means and the detector means;

that the light source means and the detector means are located in or essentially in a same plane which is parallel to the lens plane and coincident with a focal plane of the lens;

that the light source means consists of n light sources; and that the detector means consists of n cameras, where n≧2, thereby forming n light source/camera pairs to permit height dimension determination using at least two of the n cameras to provide a stereoscopic viewing of said article(s);

that all pairs, each consisting of one light source and one camera, are in the same focal plane;

that a point halfway between the light source and the camera in each pair is on the optical axis of the lens; and that the optical axis of the lens is coincident with an axis perpendicular to the focal plane and is located halfway between the light source means and the detector means.

2. An optical system according to claim 1, characterised in that each of the light sources is a point light source.

3. An optical system according to claim 1, characterised in that, with respect to the light source and the camera of a first of said pairs, and with respect to the light source and the camera of a second of said pairs, the light source of the first pair surrounds the camera lens in the second pair, and the light source in the second pair surrounds the camera lens in the first pair.

4. An optical system according to claim 3 characterised in that the light source has an annular configuration.

5. An optical system according to claim 3, characterised in that the light source consists of a plurality of point light sources.

6. An optical system according to claim 1, characterised in that an inclined, partially transparent mirror is disposed in the light path from said light source means; and that the detector means receives reflected light from the article via said mirror.

7. An optical system according to claim 1, characterised in that the pairs consisting of a light source and a camera are activated successively by a mutual time separation.

8. An optical system according to claim 1, characterised in that the light source and the camera in each pair have approximately equal aperture angles.

9. An optical system according to claim 1, characterised in that the lens is provided with an antireflection coating.

10. An optical system according to claim 1, characterised in that the lens is a Fresnel lens.

11. An optical system according to claim 5, characterised in that said point light sources are selectively activatable.

12. An optical system according to claim 5, characterised in that said point light sources emit coloured light; and
that at least some of the point light sources are arranged to emit light of different colours and/or light intensity.

13. An optical system according to claim 1, characterised in that at a point laterally displaced from and along the movement path of the article there is provided a light source and/or an inclined a mirror body tat is viewable by a camera for viewing a side portion of the articles or a crate in which the articles are placed.

14. An optical system according to claim 1, characterised in that said articles are bottles placed in a bottle crate.

15. An optical system according to claim 5, characterised in that each said point light source is a light emitting diode or a light guide.

16. An optical system according to claim 1 characterised in that the light source and the camera are positioned so as to provide for an inclination relative to said lens axis of rays propagating along said optical path.

* * * * *

UNITED STATES PATENT AND TRADEMARK OFFICE
CERTIFICATE OF CORRECTION

PATENT NO. : 7,005,629 B2  
APPLICATION NO. : 10/466892  
DATED : February 28, 2006  
INVENTOR(S) : Lennart Flem Page 1 of 1

It is certified that error appears in the above-identified patent and that said Letters Patent is hereby corrected as shown below:

Column 2
Line 61, change "show" to --shows--

Column 2
Line 62, after "cameras" insert --17' and 18' surrounded by respective light sources--

Signed and Sealed this

Twenty-second Day of August, 2006

JON W. DUDAS  
*Director of the United States Patent and Trademark Office*